United States Patent [19]

Farris et al.

[11] Patent Number: 4,761,078
[45] Date of Patent: Aug. 2, 1988

[54] DEFORMATION CALORIMETER

[76] Inventors: Richard J. Farris, 428 Chesterfield Rd., Northampton (Leeds), Mass. 01053; Richard E. Lyon, 180 Summer St., Amherst, Mass. 01002

[21] Appl. No.: 609,702

[22] Filed: May 14, 1984

[51] Int. Cl.[4] ............................................. G01K 17/00
[52] U.S. Cl. ........................................ 374/31; 374/33
[58] Field of Search ....................... 374/10, 11, 12, 31, 374/33, 13, 34; 73/717, 755

[56] References Cited

U.S. PATENT DOCUMENTS

| | | | |
|---|---|---|---|
| 1,180,665 | 8/1916 | McElroy . | |
| 3,974,930 | 7/1976 | Gizard et al. . | |
| 4,055,982 | 11/1977 | Ter-Minassian et al. | 374/10 |
| 4,072,050 | 4/1978 | Ter-Minassian . | |
| 4,130,016 | 10/1978 | Walker . | |
| 4,163,388 | 8/1979 | November | 374/37 |
| 4,306,451 | 12/1981 | Szonntagh | 374/36 |

FOREIGN PATENT DOCUMENTS 0932290  5/1982  U.S.S.R. ............................... 374/31

OTHER PUBLICATIONS

"Liquid-Gas Film Calorimeter for Deformation of Metals", the Review of Scientific Instruments, vol. 34, No. 6, pp. 639-643, Jun. 1963, R. O. Williams.
"A Calorimetric Technique for Measuring Strain Energy Released in Dicing of Stressed Glass and Glass--Ceramics", H. Stephens, E. Beauchamp, American Ceramic Society Bulletin, vol. 53, No. 2, pp. 159, 160, 167, 168, Feb. 1974.
"A Deformation Calorimeter," Robin, O. Williams, the Review of Scientific Instruments, vol. 31, No. 12, pp. 1336-1341.
"A New Method of Deformation Calorimetry", D. Ronnpagel, J. Phys. E: Sci. Instrum., vol. 12, No. 5, May 1979, pp. 409-417.
"Thermo Mechanical Studies of Polymer Deformation Part I: New Deformation Calorimeter (Duvdevani et al.-1969).
"Time Effects on the Thermochemical Behaviour of Natural Rubber" (Araimo et al.-1975).
"Thermodynamics of Reformation; Calorimetric Investigations of Deformation Processes" (Müller-1958).
"Automatic Microcalorimatic Apparatus for the Study of Thermal Process Resulting from Mechanical Deformation of Polymers" (Godovskii et al.-1968).
"Flow Calorimetry with Heat Transfer by Peltier Effect" Proc. 1st Conf., Aug., Sep. 1969, Cohen et al.
"Processing of Flux Calorimatic Signal" Proc. 1st Intern. Conf., Aug.-Sep. 1969, Brie et al.
"On the Time Lag Between Thermal Event and Measuring Signal in a Heat Flux Calorimeter" Schonborn et al.
L. Morbitzer, et al., Knoll. z. u Z. Polym., 216/217, 137 (1967).
Foster et al., Proc. Fourth Int. Cong. Rheol., Part 2, 121, Interscience, New York, 1965.
Price et al., Polymer, 14, 339 (1973).
Calvet et al., "Recent Progress in Microcalorimetry," McMillan Co., New York, 1963.
W. Zielenkiewicz, Proc. 1st Int. Conf. Calorimetry and Thermodynamics, (Warsaw), 37, Polish Scientific Publ., Poland, 1969.
Ad. Engelter and F. H. Muller, Rheol. Acta 1, 39 (1958); Ad Engelter, Dissertation, Marburg 1957.

*Primary Examiner*—William A. Cuchlinski, Jr.
*Assistant Examiner*—W. Morris Worth
*Attorney, Agent, or Firm*—Robert Shaw

[57] ABSTRACT

A deformation calorimeter that serves to deform a sample material whose temperature changes as a function of the deformation. The temperature change causes heat to flow into the material or out, depending on the character of the deformation, to cause a pressure change in a gas in and around the material. An analyzing scheme is employed to relate the pressure change to the amount of heat evolved during sample deformation.

21 Claims, 3 Drawing Sheets

DEFORMATION CALORIMETER

The present invention relates to deformation calorimeters.

By way of background, attention is called to the following writings: F. H Muller and A. Engelter, Rheol. Acta., 1. 39 (1958); Yu. K. Godovskii, G.L. Slominski and V. F. Alekseyev, Polymer Science U.S.S.R., 11(5), 1345-53 (1969); C. Price, K. A. Evans and F. de Candia, Polymer, 14 338 (1973); and I. J. Duvdevani, J. A. Biesenberger and C. G. Gogos, Polym; Eng. & Sci., 9(4), 250 (1969). Attention is also called to U.S. Pat. Nos. 4,072,050 (Ter-Minassion) and 4,130,016 (Walker).

As is pointed out in the Godovskii et al writing, deformation of materials is accompanied by thermal effects. Joule, for example, established that a rubber strip became hot when stretched and then cooled when it contracted. Conversely, a steel wire, when placed in tension, absorbs heat from the surrounding environment and liberates that heat when the tension is relieved. A careful measurement of the heat absorbed and liberated can be used by scientists to infer physical characteristics of the material deformed.

Accordingly, it is an object of the present invention to provide a deformation calorimeter which can deduce the amount of heat generated or absorbed during deformation.

Another objective is to provide an instrument which permits heat of material deformation to be estimated directly from a measured change in gas pressure in a gas surrounding the material.

These and still further objectives are addressed hereinafter.

The foregoing objectives are attained, generally, in a method of measuring heat evolved or absorbed by a sample material undergoing deformation, that comprises: deforming the sample material whose temperature changes as a function of the deformation, which temperature change causes heat to flow and effect a pressure change in a gas surrounding the material; and relating the pressure change to the amount of heat exchanged with the surroundings during sample deformation.

The invention is hereinafter described with reference to the accompanying drawing in which.

Figure 1:
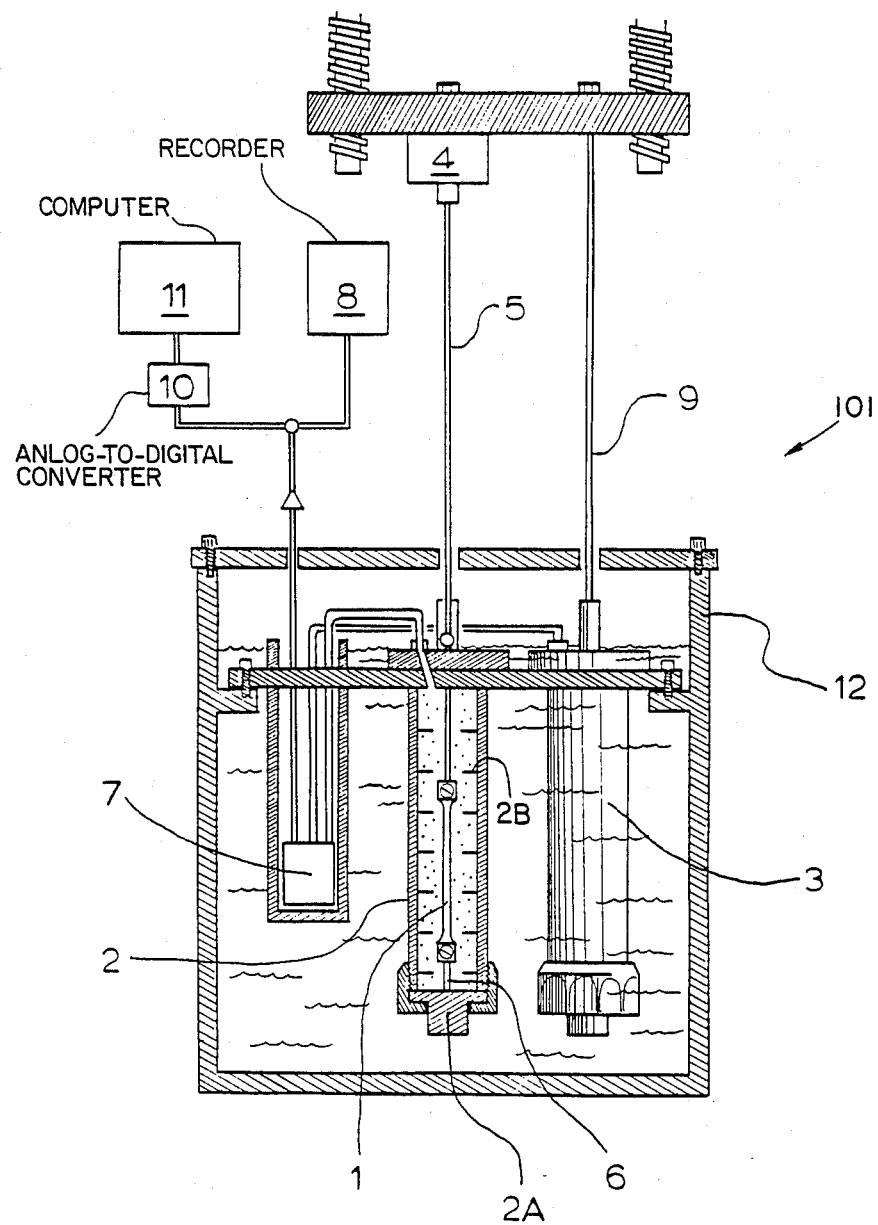
FIG. 1 is an elevation view, partly diagrammatic in form, of an instrument adapted to perform function in accordance with the present teaching.
Figure 2:
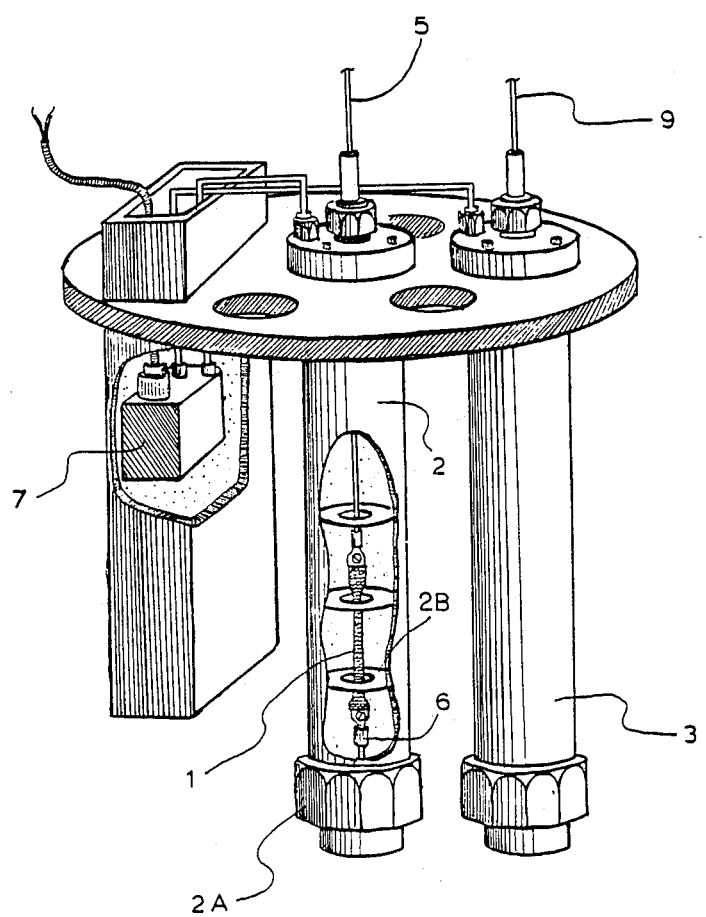
FIG. 2 is an isometric view, partly cutaway, of the operating sub-assembly of the instrument in FIG. 1.
Figure 3:
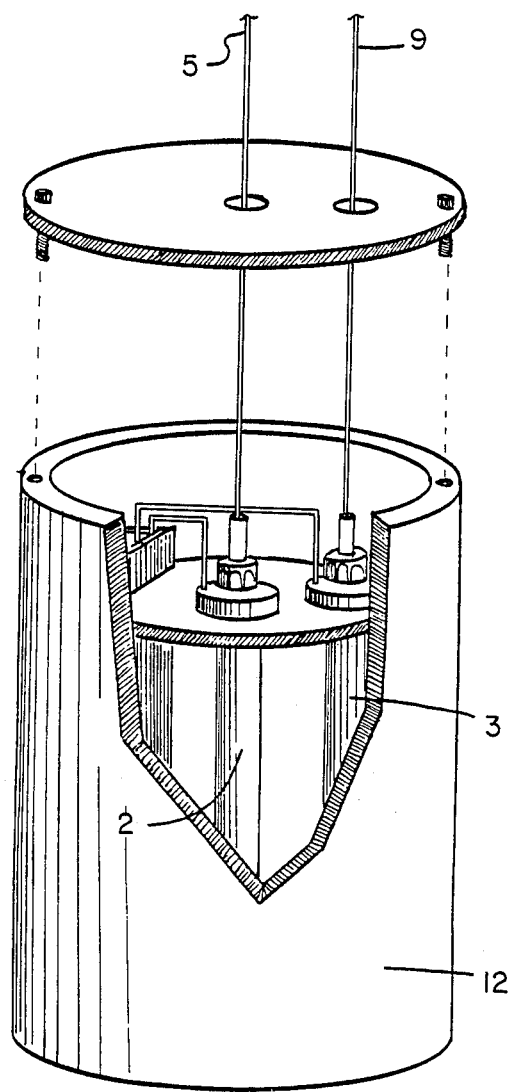
FIG. 3 is a cutaway isometric view of the entire instrument containing the sub-assembly in FIG. 2.

Turning now to the figures, the instrument shown at 101 is a deformation calorimeter for measuring heat evolved or absorbed by a sample material 1 undergoing deformation. For purposes of this discussion, let it be assumed that the sample 1 is a metal strip in tension. The calorimeter 101 consists of two sealed, gas-filled (e.g., air) chambers 2 and 3, the sample material 1 being disposed within the chamber 2. The sample is (in the disclosed embodiment) placed in tension (but can be deformed by compression) by a force between a load cell 4 and the bottom labeled 2A of the chamber 2, the force being transmitted by a pullwire (or rod) 5 to the sample which is attached by a further wire 6 to the bottom 2A. A pressure transducer 7 produces a recordable signal which is proportional to any difference in gas pressure between the chambers 2 and 3; typically the signal is a voltage which can be converted to a digital signal by an analog-to-digital converter (ADC) 10. The output of the ADC 10 is connected to a computer 11 that is programmed to relate the digital signal (which represents the differential gas pressure versus time) to the heat generated during sample deformation, as now explained. Or the transducer output can be connected to a recorder 8, as noted below.

The instrument 101 (which has been designed and built) directly measures the heat evolved or absorbed by materials undergoing deformation. The principle of measurement is fundamentally different from other instruments built for this purpose in that pressure change is employed directly to calculate the heat generated during sample deformation. The instrument 101 is unique in that it measures heat rather than temperature without the necessity of a null or compensating device; the actual device built consists of two hollow cylindrical chambers 2 and 3 which can be sealed and are in thermal contact with a constant temperature bath 12 maintained at any temperature $T_o$ (e.g. room temperature), ($T_o$ can be any temperature which one can maintain in the bath 12 using heating or cooling elements external to the bath.)

The sample 1 is attached to the bottom of the cylinder 2, as above indicated, and deformed inside the cylinder 2 via the pullwire 5 which exits the top of the cylinder through an essentially frictionless mercury seal. The cylinder 3 is identical but contains no sample although it does have a pullwire 9. The two cylinders are separated by the differential pressure transducer 7 which produces a voltage signal proportional to the difference in gas pressure between the two cylinders. This signal is recorded versus time on the suitable recorder 8, and is analyzed using the equations below to calculate the heat of sample deformation. Measurements are performed by simultaneously removing the pullwires 5 and 9 from both cylinders so as to cause no pressure difference between the cylinders due to a change in volume, i.e., constant differential volume.

The sample which is attached to the pullwire 5 will be deformed causing heat Q to flow to the gas. Since the gas is also able to exchange heat with the constant temperature cylinder walls, the net pressure change ($\Delta P$) between the cylinders is related to the difference between the rate at which heat is added to and removed from the gas in the sample chamber 2.

This may be formulated mathematically in the following way. If $Q = \partial Q/\partial t$ is the rate at which heat is generated in the sample chamber 2 by a deforming sample 1 and heat is removed through the cylinder walls according to some kernel function K(t), then the change in pressure between the sample cylinder and reference cylinder at any time is:

$$\Delta P(t) = \int_0^t K(t-\xi) \frac{\partial Q}{\partial \xi} d\xi \tag{1}$$

Experimentally it is found that for a certain cylinder geometry of the chambers 2 and 3:

$$K(t) = \frac{1}{C\tau} e^{-t/\tau}$$

In the foregoing expressions and later herein, the term Q represents heat flow into the material 1 or out of the material 1 by virtue of the deformation of the material; $\xi$ is a dummy time variable of integration; $\partial Q/\partial \xi$ is an arbitrary heat flow into or out of the material 1 resulting from the deformation process; C=thermal capacity of the calorimeter; and $\tau$=the time constant of the calorimeter.

Substituting this result into equation (1), and inverting yields the desired quantity Q(t) heat flow in terms of the measured $\Delta P(t)$ as $$Q(t) = C \int_0^t \Delta P(\xi) d\xi + C\tau \Delta P(t) \quad (2)$$

where $$\int_0^t$$

$\Delta P(\xi) d\xi$ is the area under the recorded pressure versus time curve and $\Delta P(t)$ is the value of the differential pressure at time t. Differentiating with respect to time yields the rate of heat flow from the sample as $$\frac{dQ(t)}{dt} = \dot{Q}(t) = C\Delta P(t) + C\tau \frac{d\Delta P(t)}{dt} \quad (3)$$

where $$\frac{d\Delta P(t)}{dt}$$

is the slope of the recorded differential pressure versus time curve at time t. Of primary importance is the result obtained from equation (2) when thermal equilibrium has been established following a deformation.

In this case, as $t \to \infty$, $\Delta P(t) \to 0$, and $$Q = C \int_0^\infty \Delta P(t) dt \quad (4)$$

This result is independent of the form of the kernel function K(t). Thus the total heat for the deformation process is proportional to the area under the recorded pressure-time curve after thermal equilibrium has been re-established, and this result is independent of the way in which heat was added to or removed from the system. The constants C and $\tau$ are determined experimentally and are characteristic of the cylinder geometry.

The desired quantities Q(t), $$\frac{dQ(t)}{dt}$$

and Q are calculated from the recorded pressure-time curve using equations 2, 3 and 4, respectfully. In practice this has been accomplished by performing integrations and derivatives of the actual pressure versus time data using graphical or electronic methods.

The chambers 2 and 3, in actual test apparatus, are stainless steel, circular cylinders whose inside diameter is 1.9 centimeters (¾") and whose height is 7–25 centimeters. The gas in the cylinders is air which is about at atmospheric pressure when the cylinders are sealed. A water bath at about 25 degrees celsius (or any temperature obtainable by external heating or cooling of the bath) provides an isothermal environment within the chambers. The pressure transducer 7 actually employed is a Celesco P7D differential pressure transducer; it can measure pressure differentials of 0.1 psi full scale at 10 volts and the total apparatus can sense heat as low as the order of 100 microcalories. It is an important aspect of the present invention, to satisfy the kernel function K(t) in the above expressions, that the chambers be vertically-oriented and cylindrical, that the sample (and hence the wires or rods) be at or near the vertical axis of the sample cylinder, and that the thermal constants of the sample plus that of the wires and rods be small compared to the thermal constants of the gas within the cylinders. Also, the chambers 2 and 3 should be the same size; their horizontal baffles (e.g., 2B) made of thin polymer films are positioned vertically at regular intervals within the chambers to eliminate unwanted dependence of differential gas pressure on the position of the material sample being deformed therein.

A further few comments are included in this and the next paragraph. The relationship between differential gas pressure and heat flow from or to the sample are related through simple linear hereditary integral equations or, equivalently, linear differential equations which can be easily solved to yield equations for heat flow between the sample and the gas in the chamber 2. The kernel function in the linear hereditary integral equation or the coefficients in the linear differential equations can be determined by calibration.

Calibration of experimental apparatus involved placing an electric heating unit into the chamber 2 and introducing known wattages thereto. The effect on gas pressure was then recorded and analyzed graphically to provide the numerical value of the constants C and $\tau$ in the above expressions. Once C and $\tau$ are known, the heat generated during sample deformation experiments can be calculated using any of equations 2, 3, or 4 above.

Further modification of the invention herein disclosed will occur to persons skilled in the art and all such modifications are deemed to be within the scope of the invention as defined by the appended claims.

What is claimed is:

1. Apparatus for measuring heat flow between a material undergoing deformation and its surrounding environment, that comprises:
   a plurality of gas-filled, sealed chambers;
   means in one chamber for securing the material to undergo deformation therein;
   force means to effect deformation of said material, which deformation generates heat Q which flows to the gas in said one chamber;
   means to produce a recordable signal which is proportional to any time-related difference in gas pressure between said chambers as a result of the heat flow in said one chamber, said difference in gas pressure being related to said heat generated in said materials by either a linear hereditary equation or a linear differential equation that is solved to yield equations for heat flow between the material and the gas; and
   analyzing means connected to receive the recordable signal and operable to analyze the recordable signal to relate said time-related difference in gas pressure to heat generated in the material and thereby provide a direct determination of heat flow in accordance with the expression $$\Delta P(t) = \int_0^t K(t-\xi)\frac{\partial Q}{\partial \xi} d\xi,$$

wherein t is time, ΔP(t) is differential gas pressure resulting from said heat flow as a function of the time t, K(t) is a kernel function which is dependent on the geometry of the chamber and $\partial Q/\partial \xi$ is an arbitrary heat flow into or out of the material as a result of said deformation.

2. Apparatus as claimed in claim 1 wherein the environment surrounding the chambers is an isothermal environment at room temperature and wherein the gas-filled, sealed chambers are at about atmospheric pressure.

3. Apparatus as claimed in claim 2 wherein the isothermal environment is a constant temperature bath which is maintained at its temperature through suitable heating or cooling means.

4. Apparatus as claimed in claim 1 wherein said means to produce a recordable signal is a differential pressure transducer.

5. Apparatus as claimed in claim 1 wherein said force means is a pullwire or rod, said pullwire or rod being attached to said material to be deformed, said pullwire or rod exiting from said chamber through a low-friction mercury seal, the thermal mass of the material and the pullwire or rod being small with respect to other factors in the environment around the material.

6. A method of measuring heat flow relative to a sample material undergoing deformation in a hollow gas-filled enclosure, that comprises:
   measuring and recording differential gas pressure due to a calibrated heat source at constant volume in the hollow gas-filled enclosure in the absence of the sample material;
   securing the sample material to be deformed in the gas within the hollow enclosure;
   sealing and immersing said hollow enclosure within an isothermal environment;
   deforming said sample material; and
   measuring and recording any gas pressure differential ΔP within said hollow gas-filled enclosure during deformation of said sample material and relating said gas pressure differential ΔP, as a function of time t, directly to heat Q generated by the sample material during deformation using linear hereditary relationships to thereby provide a direct determination of heat flow, said linear hereditary relationships being in the form of the following expression $$\Delta P(t) = \int_0^t K(t-\xi)\frac{\partial Q}{\partial \xi} d\xi,$$

wherein K(t) is a kernel function which is dependent on the geometry of said enclosure, $\xi$ is the time variable of integration and $\partial Q/\partial \xi$ is an arbitrary heat flow into or out of the sample resulting from the deformation process.

7. Apparatus for measuring heat flow with respect to a material undergoing deformation thereby to provide heat of deformation with respect to said material, that comprises:
   a first sealed gas-filled chamber and a second sealed gas-filled chamber, each chamber containing a movable wire or rod which exits through a low-friction gas-tight seal from the chamber, the wire or rod in the first gas-filled chamber being adapted to attach to the material within the gas, there being means in the first gas-filled chamber for securing the material to apply a force thereto by the wire or rod to effect deformation of said material by the transmission of the force to provide said heat of deformation;
   a differential gas pressure transducer connected between the first gas-filled chamber and the second gas-filled chamber, which differential gas pressure transducer is operable to produce a signal which is proportional to any difference ΔP in gas pressure between said first gas-filled chamber and said second gas-filled chamber;
   means to insure that the gas pressure difference ΔP measured during material deformation is independent of the position of said material in said first gas-filled chamber;
   means to insure that the gas pressure difference measured during material deformation is not the result of a differential volume change in the gas in said first gas-filled chamber and said second gas-filled chamber caused by displacing the pullwire or rod attached to the material being deformed; and
   analyzing means to relate directly differential gas pressure versus time relationship to the heat flow during deformation of said material in said apparatus to permit determination of the heat of deformation directly from the measured change in gas pressure in said first chamber in the gas surrounding said material, said analyzing means being operable to relate said differential gas pressure ΔP at any time t, ΔP(t), such that the rate of heat generation $\partial Q/\partial \xi$ is given by the equation $$\Delta P(t) = \int_0^t K(t-\xi)\frac{\partial Q}{\partial \xi} d\xi,$$

wherein where K(t) is a kernel function which is dependent on the geometry of said first gas-filled chamber, $\xi$ is the time variable of integration, and $\partial Q/\partial \xi$ is an arbitrary heat flow into or out of the sample resulting from the deformation process.

8. Apparatus as claimed in claim 7 wherein the environment surrounding said chambers is an isothermal environment.

9. Apparatus as claimed in claim 8 wherein the isothermal environment is a constant temperature bath.

10. Apparatus as claimed in claim 7 wherein said force is transmitted by said wire or rod, said wire or rod attaching to said material to be deformed, and said wire or rod further exiting from said gas-filled chamber through a frictionless gas-tight seal.

11. Apparatus as claimed in claim 7 wherein both said first sealed gas-filled chamber and said second gas-filled chamber are at about atmospheric pressure.

12. Apparatus as claimed in claim 7 wherein differential gas pressure changes caused by differential volume changes are eliminated by simultaneously displacing wires or rods which exit from both chambers.

13. Apparatus as claimed in claim 7 wherein thin horizontal baffles are positioned vertically at regular intervals in said chambers to eliminate unwanted dependence of differential gas pressure on position of the material to be deformed in said chambers.

14. Apparatus as claimed in claim 7 in which said low-friction gas-tight seal is a mercury drop at the point of exit of each said wire or rod from each said gas-filled chamber.

15. Apparatus according to claim 7 wherein said equation is changed to the following:

$$Q = C \int_0^\infty \Delta P(t) \, dt,$$

wherein C is the thermal capacity of said apparatus.

16. Apparatus according to claim 7 in which the kernel function K(t) in said expression is given by $$K(t) = \sum_{i=1}^{n} \frac{e^{-t/\tau_i}}{C_i \tau_i},$$

wherein C is the thermal capacity of said apparatus and $\tau$ is the time constant of said apparatus.

17. Apparatus according to claim 16 wherein the kernel function K(t) is achieved in said apparatus in a structure wherein the two chambers have a cylindrical geometry and there is only a very small thermal mass within the first chamber, that is, the material and the wire or rod must be small in relationship to the gas volume within the first chamber.

18. Apparatus according to claim 7 in which said differential gas pressure and heat flow in said material are related through a linear hereditary integral equation which is solved to yield equations for heat flow between the material and a gas and in which the kernel function of the linear hereditary integral equation is determinable by calibration of the apparatus.

19. Apparatus according to claim 7 in which said differential gas pressure and heat flow in said material are related through a linear differential equation which is solved to yield equations for heat flow between the material and the gas and in which the constants of the linear differential equation are determinable by calibration of the apparatus.

20. A calorimeter for measuring heat flow relative to a sample material undergoing deformation, that comprises:

a hollow gas-filled and sealable chamber;
means for securing the sample material to be deformed in the gas within the hollow chamber;
means for deforming said sample material; and
means for measuring and recording any gas pressure differential $\Delta P$ within said hollow gas-filled chamber during deformation of said sample material and relating said gas pressure differential $\Delta P$, as a function of time t, directly to heat Q generated by the sample material during deformation using linear hereditary relationships to thereby provide a direct determination of heat flow, said linear hereditary relationships being in the form of the following expression $$\Delta P(t) = \int_0^t K(t - \xi) \frac{\partial Q}{\partial \xi} \, d\xi,$$

wherein K(t) is a kernel function which is dependent on the geometry of said hollow chamber, $\xi$ is the time variable of integration and $\partial Q/\partial \xi$ is an arbitrary heat flow into or out of the sample resulting from the deformation process.

21. A calorimeter for measuring heat flow relative to a sample material undergoing deformation, that comprises:

a hollow gas-filled and sealable chamber;
means for securing the sample material to be deformed in the gas within the hollow chamber;
means for deforming said sample material; and
means for measuring and recording any gas pressure differential $\Delta P$ within said hollow gas-filled chamber during deformation of said sample material and relating said gas pressure differential $\Delta P$, as a function of time t, directly to heat Q generated by the sample material during deformation, to thereby provide a direct determination of heat flow using the following expression $$Q = C \int_0^\infty \Delta P(t) \, dt,$$

wherein C is a constant representative of the thermal capacity of the calorimeter.

* * * * *